Figure 1:
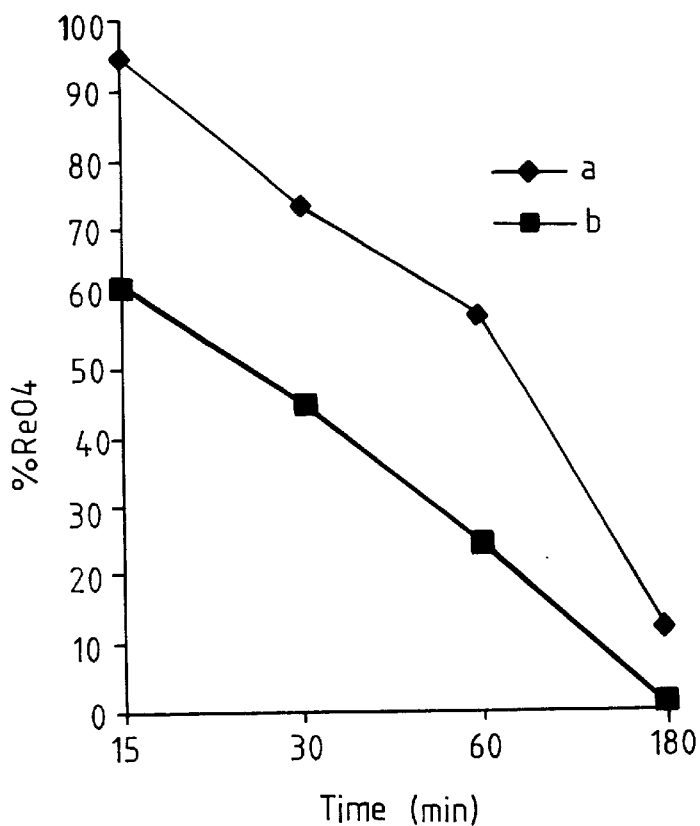

United States Patent [19]
Duatti et al.

[11] Patent Number: 6,127,530
[45] Date of Patent: Oct. 3, 2000

[54] METHOD FOR THE REDUCTION OF OXYGENATED COMPOUNDS OF RHENIUM OR TECHNETIUM

[75] Inventors: Adriano Duatti, Chiesuol Del Fosso; Cristina Bolzati, Jolanda Di Savoia; Licia Uccelli, Ferrara; Rodolfo Franceschini, Pisa; Alessandra Boschi, San Lazzaro Di Savena, all of Italy

[73] Assignee: Nycomed Amersham Sorin S.r.l., Milan, Italy

[21] Appl. No.: 09/269,898

[22] PCT Filed: Oct. 3, 1997

[86] PCT No.: PCT/EP97/05448

§ 371 Date: Jun. 4, 1999

§ 102(e) Date: Jun. 4, 1999

[87] PCT Pub. No.: WO98/14219

PCT Pub. Date: Apr. 9, 1998

[30] Foreign Application Priority Data

Oct. 3, 1996 [IT] Italy .................... T96A0805

[51] Int. Cl.⁷ .................... A61K 51/04; A61K 47/06; C07F 13/00
[52] U.S. Cl. .................... 534/10; 424/1.53; 424/1.11; 514/777; 514/778; 534/14; 536/46; 536/103
[58] Field of Search .................. 424/1.11, 1.53; 514/777, 778; 536/103, 46; 534/10, 14

[56] References Cited

U.S. PATENT DOCUMENTS 5,300,280  4/1994  Derosch et al. .................... 424/1.53

FOREIGN PATENT DOCUMENTS

| | | | |
|---|---|---|---|
| 0 311 891 | 4/1989 | European Pat. Off. ........ | C07F 13/00 |
| 95 08606 | 1/1997 | France ........................... | A61K 51/00 |
| 265 628 A1 | 3/1989 | Germany ........................ | C07F 13/00 |
| 53-095950 | 8/1978 | Japan .............................. | C07F 1/08 |
| 59-145037 | 8/1984 | Japan .............................. | B01J 13/00 |
| WO 93/15765 | 8/1993 | WIPO ............................ | A61K 43/00 |

OTHER PUBLICATIONS

Alberto et al., "New organometallic technetium complexes in high and low oxidation states," *Radiochimica Acta*, 63, 153–161 (1993).

Hermann et al., "Mehrfachbindungen zwischen Hauptruppenelementen und Übergangsmetallen," *Journal of Organometallic Chemistry*, 372, 351–370 (1989).

Haby et al., "Development of a stable single–vial formulation for a new technetium complex using bilayer lyophilization," *PDA Journal of Pharmaceutical Science & Technology*, vol. 51, No. 2, 68–71 (1997).

*Primary Examiner*—Joseph McKane
*Assistant Examiner*—Ebenezer Sackey
*Attorney, Agent, or Firm*—Marshall, O'Toole, Gerstein, Murray & Borun

[57] ABSTRACT

The present invention relates in general to a method for the reduction of oxygenated compounds of rhenium and technetium and in particular to the reduction of perrhenate or pertechnetate ions.

More particularly, the invention relates to reactions for the reduction of the said oxygenated compounds which are carried out in the course of the preparation of complexes of the radionuclides $^{186}$Re, $^{188}$Re and $^{99m}$Tc; in these reactions, the radionuclide perrhenate or pertechnetate ion is reduced in the presence of a reducing agent and a ligand which can form a complex with the radionuclide in its reduced oxidation state.

15 Claims, 2 Drawing Sheets

METHOD FOR THE REDUCTION OF OXYGENATED COMPOUNDS OF RHENIUM OR TECHNETIUM

This application is a 371 of PCT/EP97/05448 filed Oct. 3, 1997.

The present invention relates in general to a method for the reduction of oxygenated compounds of rhenium and technetium and in particular to the reduction of perrhenate or pertechnetate ions.

More particularly, the invention relates to reactions for the reduction of the said oxygenated compounds which are carried out in the course of the preparation of complexes of the radionuclides $^{186}$Re, $^{188}$Re and $^{99m}$Tc; in these reactions, the radionuclide perrhenate or pertechnetate ion is reduced in the presence of a reducing agent and a ligand which can form a complex with the radionuclide in its reduced oxidation state.

It is known that the radionuclides $^{186}$Re, $^{188}$Re and $^{99m}$Tc have nuclear properties which make their coordination compounds suitable for application in nuclear medicine as therapeutic and diagnostic agents. Although the similarity between the chemical properties of technetium and rhenium lead one to think that a method of synthesising $^{99m}$Tc radiopharmaceuticals might simply be transferred to the preparation of similar tracers of $^{186}$Re and $^{188}$Re, there are, however, fundamental differences between the properties of the two elements such as to make the possible use of rhenium compounds in nuclear medicine subject to certain conditions.

In fact, since the metals technetium and rhenium in their highest oxidation states and, in particular, the tetraoxygenated anions $[MO_4]^-$ (M=Re, Tc) are the principal starting materials for the synthesis of radiopharmaceuticals of rhenium and technetium, the result is that the reduction potentials of these species play a very important role in determining the course of the synthesis reactions. In particular, it is known that the reduction potential of the pertechnetate anion is considerably greater than that of the perrhenate anion. This indicates that, once a given synthesis has been determined, it must be much easier to prepare a technetium complex than the analogous rhenium complex.

In general, it is possible for a given synthesis adopted to obtain a radiopharmaceutical from $^{99m}$Tc give a very much lower reaction yield in the case of rhenium. This conclusion is even more significant when one considers that, in the therapeutic application of rhenium compounds, the final product must have a very high radiochemical purity to reduce radiological risks.

The considerations set out above show that, to produce radiopharmaceutical preparations involving metal complexes of the radionuclides $^{186}$Re and $^{188}$Re, it is necessary to provide a method of synthesis which is very efficient at reducing the perrhenate ion.

U.S. Pat. No. 4,455,291 discloses that various "accelerators" are useful to facilitate the preparation of cationic $^{99m}$Tc complexes. Accelerators include oxalic acid, tartaric acid and ascorbic acid.

U.S. Pat. No. 4,871,836 discloses that $^{186}$Re/$^{188}$Re kits can usefully contain an "accelerator (catalyst)", preferably citric acid, tartaric acid and malonic acid. Example 9 discloses a freeze-dried kit for the preparation of $^{186}$Re complexes from perrhenate which includes both citric acid and cyclodextrin in the formulation. The cyclodextrin is described as a solubiliser.

U.S. Pat. No. 5,026,913 discloses that cyclodextrins can be used as solubilisers in kits for the preparation of $_{99m}$Tc radiopharmaceuticals.

U.S. Pat. No. 5,300,280 discloses a method of stabilising radiopharmaceutical kits using cyclic oligosaccharides (cyclodextrins) to inhibit oxidation and/or volatilisation of the kit components. $^{186}$Re, $^{188}$Re and $^{99m}$Tc are specifically claimed.

DD 265628 discloses a method for the production of in vivo stable $^{99m}$Tc pertechnetate crown ether coordination compounds, wherein crown ethers are reacted stoichiometrically with $Sn^{2+}$ cations and sodium $_{99m}$Tc-pertechnetate is added in a stoichiometric amount.

A specific object of the present invention is to provide a more efficient method for the reduction of oxygenated compounds of rhenium and, in particular, of the perrhenate ion.

Another object is to provide a general method of synthesis of radiopharmaceuticals of rhenium, applicable to the preparation of different classes of compounds under sterile and apyrogenic conditions.

With reference to technetium, although its reduction potential is more favourable than that of rhenium, its reduction in the presence of specific ligands'to form a complex may be very difficult depending upon the specific ligand used. For this reason, there is also a need to provide a more efficient method of reducing technetium which facilitates the formation of the desired complex without the need to adopt particularly drastic reduction conditions and a further object of the present invention results from this need.

In view of the aforesaid objects, a subject of the present invention is a method for the reduction of oxygenated compounds of rhenium or technetium, carried out in the presence of a reducing agent, wherein the reduction is carried out in the presence of a macromolecular compound selected from the group consisting of cyclic oligosaccharides, crown ethers and cryptands, said macromolecular compound being effective to displace the equilibrium of the reduction reaction toward the formation of the reduced species of the rhenium or technetium.

The reduction process to which the invention relates, makes use of the supramolecular interactions known as host-guest interactions. It is known that a host-guest interaction consists of the formation of a supramolecular aggregate of two species, of which the first (host) is characterised by the presence of a molecular cavity sufficiently large to house the second (guest) which is of smaller dimensions. The forces which cause the smaller molecule to be trapped generally belong to the category of weak interactions (van der Waals interactions, hydrogen bonding, hydrophilic and hydrophobic interactions, London forces) and thus do not alter the chemical nature of the species enclosed in the cavity.

The host molecules used in the process of the invention include cyclic oligosaccharides such as, in particular, modified or unmodified cyclodextrins, crown ethers and cryptands.

The modified or unmodified cyclodextrins usable in the invention include α-cyclodextrins, β-cyclodextrin, γ-cyclodextrin and their mixtures. γ-cyclodextrins are particularly preferred.

By way of example, hydroxypropyl-α-cyclodextrin and hydroxyethyl-α-cyclodextrin may be used as the α-cyclodextrin; hydroxypropyl-β-cyclodextrin, carboxymethyl-β-cyclodextrin, dihydroxypropyl-β-cyclodextrin, hydroxyethyl-β-cyclodextrin, 2,6-di-o-methyl-β-cyclodextrin and sulphated β-cyclodextrin may be used as the β-cyclodextrin; hydroxypropyl-γ-cyclodextrin, dihydroxypropyl-γ-cyclodextrin; hydroxypropyl-γ-cyclodextrin and sulphated γ-cyclodextrin may be used as the γ-cyclodextnin.

A full review of the cyclodextrins usable as host molecules in supramolecular structures is provided in the article by G. Wenz in Angew, Chem. Int. ed. engl., 1994, 33, 803–822 incorporated herein by reference.

As crown ethers there may be used crown ethers available commercially and their derivates such as, for example, the compounds given in the Fluka 1995/96 catalogue, p 419, among which in particular are the 12-crown-4, 15-crown-5 and 18-crown-6 ethers and their derivatives.

It is understood that, in embodiments of the invention which relate to the production of radiopharmeceutical complexes, the host molecules used must be pharmaceutically acceptable.

The quantity of host molecule used in the process of the invention is not particularly critical and is generally in the stoichiometric ratio or in excess with respect to the rhenium or technetium. The reducing agents which may be used within the scope of the invention are any reducing agents able to reduce the compound or anion of rhenium or technetium. The preferred reducing agents for the perrhenate and pertechnetate anions comprise $Sn^{2+}$, $Fe^{2+}$ and $Cu^{1+}$, of which the stannous ion, which is widely used in radiopharmaceutical preparations, is preferred. These ions may be introduced into the reaction medium in the form of halides, particularly the chlorides, or in the form of inorganic salts such as phosphonates and organic salts, particularly salts of polycarboxylic acids, such as tartrates, citrates, oxalates, gluconates and glucoheptanates. Other reducing agents include phosphines, such as triphenylphosphine, tris(2-sulphonatophenyl)phosphine, tris(cyanoethyl)phosphine, sodium borohydride, alkali metal thiosulphates, dithionites and dithionates.

According to a preferred embodiment, the reduction reaction is carried out in the presence of a polycarboxylic acid or metal salt thereof (preferably an alkali metal salt), such as oxalate, citrate, ascorbate, malonate or tartrate, which acts as a secondary reducing agent. Oxalate is highly preferred.

The ligands used in the invention include ligands used in radiopharmaceutical kits such as, for example, phosphines, phosphonates, arsines, thiols, thioethers, isonitriles, amines, cyclic amines, polyamines, dithiocarbamates, dithiocarboxylates, Schiff bases, diaminodithiols, bis(amino)thiols, oximes, sugars, borates, amino acids, polyamino acids, ligands including combinations of these groups and peptide ligands. In general the ligand may comprise any molecule that has atoms which are able to coordinate with the central rhenium or technetium metal ion to form a stable complex or a complex which can give rise to substitution reactions with other ligands.

It is also possible to use the methods described in the invention to produce radiopharmaceuticals of $^{186}Re$ and $^{188}Re$, characterised by the presence, in the structure of the complex, of the terminal rhenium-nitride triple bond, Re≡N, through the use of suitable donor molecules of nitride groups $N^{3-}$ such as hydrazine, hydrazine derivatives, derivatives of dithiocarbazic acid, sodium azide and, in general, molecules containing the functional >N—N< group.

One embodiment of the invention includes the choice of coordinating ligands which satisfy one or both of the following requisites:
a) the ligand fused promotes the stabilisation of the reduced species which forms as a result of the reduction of the perrhenate or pertechnetate ion; and
b) forms a complex with the reduced species which can give rise to a substitution reaction with other ligands.

The requisite b) takes account of the fact that the coordination compound produced by the method given by the above process, and containing the metal ion in a lower oxidation state, in turn constitutes a pre-reduced intermediate through which it is possible to obtain the final complexes by means of simple substitution reactions. In this embodiment, it is preferable to use ligands, such as oxalate and citrate, in the reduction reaction which are able to promote the electroreduction of the $[ReO_4]^-$ anion and which do not give rise to stable complexes with rhenium, particularly in oxidation states less than +7.

In this embodiment, the reaction is carried out in the presence of a first ligand which satisfies requirements a) and b), particularly oxalate and citrate, and a second ligand suitable for the preparation of a specific radiopharmaceutical and capable of replacing completely the first ligand which coordinates weakly with the metal centre (i.e. ligand displacement or transchelation).

Examples of phosphine ligands for use in radiopharmaceutical kits include tris(3-ethoxypropyl)phosphine, trimethylphosphine, triethylphosphine, tris(3-methoxy-3-methylbutyl)phosphine, tris(3-methoxypropyl)phosphine, tris[2-[2(1,3-dioxanyl)]]ethylphosphine, methylbis(3-methoxypropyl)phosphine, tris(4-methoxybutyl)phosphine, dimethyl(3-methoxypropyl)phosphine, methylbis[2-[2-(1,3-dioxanyl)]]ethylphosphine and bis(1,2-dimethylphosphine)ethane.

As peptide ligands there may, for example, be used the peptides modified with a phosphine group described in European Patent Application EP-A-0 659 764 in the name of the Applicant incorporated herein by reference.

The reduction reaction is generally carried out at a pH of between 1 and 10, preferably at a physiological pH of between 5 and 8, more preferably at a pH of from 5 to 6.

The possibility of working at a physiological pH, with a good yield, is a further advantage of the method of the invention.

The method of the invention will be further described by means of the following examples and appended drawings. In the drawings:

FIG. 1) shows time-activity curves representing the variation of the percentage of $[^{188}ReO_4]^-$ activity in the course of the reactions:
(a) $[^{188}ReO_4]^- + SnCl_2(0.2\ mg) \rightarrow [^{188}ReO(DMSA)_2]^-$ and
(b) $[^{188}ReO_4]^- + SnCl_2(0.2\ mg) \rightarrow +\gamma\text{-cyclodextrin}(10\ mg) \rightarrow [^{188}ReO(DMSA)_2]^-$ FIG. 2) shows time-activity curves representing the variation of the percentage of $[^{188}ReO_4]^-$ activity in the course of the reactions:
(a) $[^{188}ReO_4]^- + SnCl_2(1.0\ mg) \rightarrow [^{188}ReO(DMSA)_2]^-$ and
(b) $[^{188}ReO_4]^- + SnCl_2(1.0\ mg) + \gamma\text{-cyclodextrin}(10\ mg) \rightarrow [^{188}ReO(DMSA)_2]^-$ FIG. 3) shows time-activity curves representing the variation of the percentage of $[^{188}ReO_4]^-$ activity in the course of the reactions:
(a) $[^{188}ReO_4]^- + SnCl_2(0.2\ mg) \rightarrow [^{188}ReO(DMSA)_2]^-$ and
(b) $[^{188}\ ReO_4]^- + SnCl_2(1.0\ mg) + \gamma\text{-cyclodextrin}(10\ mg) + \text{oxalate}(6\ mg) \rightarrow [^{188}ReO(DMSA)_2]^-$

EXAMPLE 1

To a vial containing 2.5 mg of dimercaptosuccinic acid (DMSA below), 10.0 mg of γ-cyclodextrin and 92.0 mg of potassium oxalate were added 1.0 mg of $SnCl_2.2H_2O$ dissolved in 0.10 ml of an aqueous solution of acetic acid (20% v/v), which was followed by the addition of 0.4 ml of an aqueous solution of acetic acid (20% v/v) and 0.250 ml of saline. To the resulting solution were added 0.250 ml of a solution eluted from a [$^{188}$Re][ReO$_4$]$^-$ generator (activity in the range 50 to 500 MBq) (pH =5.5) and the vial was kept at ambient temperature (or at 100° C.). The formation of the final complex [$^{186}$ReO(DMSA)$_2$]$^-$ occurred almost instantaneously, with a radiochemical yield of more than 95%.

In the present example and in the following the resulting products were characterised by HPLC and TLC.

EXAMPLE 2

The procedure given in Example 1 was carried out in exactly the same way with the addition, however, of 0.2 mg of SnCl$_2$.2H$_2$O; the final complex formed almost instantaneously with a radiochemical yield of more than 95%.

EXAMPLE 3

The procedure of Example 1 was carried out in exactly the same way with the use, however, of 0.02 mg of SnCl$_2$H$_2$O; the formation of the final product was complete after fifteen minutes with a radiochemical yield of more than 95%.

EXAMPLE 4

To a vial containing 10.0 mg of γ-cyclodextrin and 92.0 mg of potassium oxalate were added 1.0 mg of SnCl$_2$.2H$_2$O dissolved in 0.10 ml of an aqueous acetic acid solution (20% v/v), with the subsequent addition of 0.40 ml of aqueous acetic acid solution (20% v/v) and 0.250 ml of saline. Subsequently there were added 0.250 ml of a solution eluted from a generator of [$^{188}$Re][ReO$_4$]$^-$ (activity in the range 50 to 500 MBq) (pH =5.5) and the vial was kept at ambient temperature (or at 100° C.) for fifteen minutes. Finally there were added 1.25 mg of DMSA and the resulting mixture was kept at ambient temperature (or at 100° C.). The formation of the final product [$^{186}$ReO(DMSA)$_2$]$^-$ was complete almost instantaneously with a radiochemical yield of more than 95%.

EXAMPLE 5

The procedure of Example 4 was repeated in an identical manner, with the addition, however, of 0.2 mg of SnCl$_2$.2H$_2$O. The formation of the final product was complete almost instantaneously with a radiochemical yield of more than 95%.

EXAMPLE 6

The procedure of Example 4 was carried out in an identical manner with the addition, however, of 0.02 mg of SnCl.2H$_2$O. The formation of the final product was complete after one hour with a radiochemical yield of more than 90%.

EXAMPLES 7–13

The procedures of examples 1 to 6 were repeated in an identical manner with the use, however, of the ligands 3,6-diaza-1,8-octandithiol and 3,7-diaza-1,9-nonadithiol instead of the DMSA. The radiochemical yields were greater than 95% in all tests.

EXAMPLE 14
Preparation of [$^{188}$ReO(L)Cl]

To a vial containing 3.0 mg of LH$_2$(LH$_2$=3-diphenylphosphinopropionylglycyl-L-(S-benzyl)cysteinyl methyl ester) dissolved in 0.10-ml of methanol, 10.0 mg of γ-cyclodextrin and 92.0 mg of potassium oxalate, there were added 1.0 mg off SnC$_2$.2H$_2$O dissolved in 0.20 ml of an aqueous acetic acid solution (20% v/v), with a subsequent addition of 0.30 ml of aqueous acetic acid (20% v/v). To the resulting mixture were added finally 0.500 ml of a solution eluted from a generator of [$^{188}$Re][ReO$_4$]$^-$ (activity in the range 50 to 500 MBq) (pH =5.5) and the vial was kept at ambient temperature (or at 100° C.) for one hour. The formation of the final product gave a radiochemical yield of more than 95%.

EXAMPLE 15

The procedure of Example 14 was repeated in exactly the same way with the addition, however, of 0.2 mg of SnCl$_2$.2H$_2$O. The formation of the final product gave a radiochemical yield of more than 95%.

EXAMPLE 16
Preparation of [$^{188}$Re(O)(DMSA)$_2$]$^-$

To a vial containing 6.0 mg of tris(2-sulphonatophenyl) phosphine sodium salt (TPPTS =[P(C$_6$H$_4$SO$_3$)$_3$]Na$_3$), 10.0 mg of γ-cyclodextrin, 92.0 mg of potassium oxalate, 0.50 ml of an aqueous acetic acid solution (20% v/v) and 0.250 ml of saline, there were added 0.250 ml of a solution eluted from a generator of [$^{188}$Re][ReO$_4$]$^-$ (activity in the range 50 to 500 MBq) (pH =5.0) and the vial was kept at ambient temperature (or at 100° C. respectively) for thirty minutes. There were then added 1.25 mg of DMSA and the resulting mixture was maintained at 100° C. for thirty minutes. The formation of the final product gave a radiochemical yield of more than 95%.

EXAMPLE 17
Preparation of [$^{188}$Re(O)(DMSA)$_2$]$^-$ 0.2 mg of SnCl$_2$ (dissolved in 0.5 mL of 20% aqueous glacial acetic acid), 10.0 mg of γ-cyclodextrin, 30.0 mg of sodium oxalate and 2.5 mg of H$_2$DMSA were placed in a vial followed by 0.250 mL of [$^{188}$ReO$_4$]$^-$(50 MBq–500 MBq). The vial was kept at room temperature for 15 min. Yield>95%.

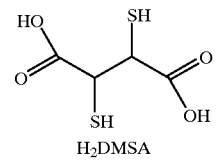
H$_2$DMSA

EXAMPLE 18
Preparation of [$^{188}$Re(O)(BAT)]

0.2 mg of SnCl$_2$ (dissolved in 0.5 mL of 20% aqueous glacial acetic acid), 10.0 mg of γ-cyclodextrin, 30.0 mg of sodium oxalate and 2.0 mg of H$_3$BAT were placed in a vial followed by 0.250 mL of [$^{188}$ReO$_4$]$^-$(50 MBq–500 MBq). The vial was kept at room temperature for 15 min. Yield>95%.

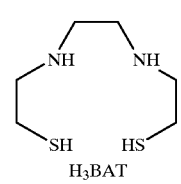
H$_3$BAT

EXAMPLE 19

Preparation of [$^{188}$Re(O)(L)Cl]

0.2 mg of SnCl$_2$ (dissolved in 0.5 mL of 20% aqueous glacial acetic acid), 10.0 mg of γ-cyclodextrin, 30.0 mg of sodium oxalate and 3.0 mg of LH$_2$ were placed in a vial followed by 0.250 mL of [$^{188}$ReO$_4$]$^-$ (50 MBq–500 MBq). The vial was kept at room temperature for 30 min. Yield>95%.

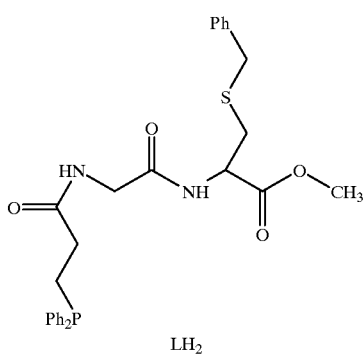

LH$_2$

EXAMPLE 20

Preparation of [$^{188}$Re(O)(P$_2$N,)C ]

0.2 mg of SnCl$_2$ (dissolved in 0.5 mL of 20% aqueous glacial acetic acid), 10.0 of γ-cyclodextrin 30.0 mg of sodium oxalate and 3.0 mg of P$_2$N$_2$H$_2$ were placed in a vial followed by 0.250 mL of [$^{188}$ReO$_4$]$^-$ (50 MBq–500 MBq). The vial was kept at room temperature for 15 min. Yield>95%.

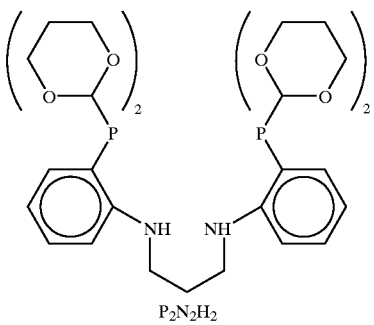

P$_2$N$_2$H$_2$

EXAMPLE 21

Preparation of [$^{188}$Re(N)(DEDC)$_2$]

0.2 mg of SnCl$_2$ (dissolved in 0.5 mL of 20% aqueous glacial acetic acid), 10.0 of γ-cyclodextrin 30.0 mg of sodium oxalate and 1.0 mg of N-methyl, S-methyl dithiocarbazate (H$_2$NN(CH$_3$)C(S)SCH$_3$ were placed in a vial followed by 0.250 mL of [$^{188}$ReO$_4$]$^-$(50 MBq–500 MBq). The vial was kept at room temperature for 15 min. Successively, 5.0 mg of diethylenetriaminopentaacetic acid (DTPA) and 10.0 mg of the sodium salt of diethyldithiocarbamate (DEDC or [Et$_2$NCS$_2$]Na) were added, and the vial was heated at 100 for 5 min. Yield>95%.

NaDEDC

Other preparations have been carried out by adding the host molecule and the secondary reducing agent Red to a commercial kit formulation of a specific ligand before labelling with [$^{188}$ReO$_4$]. This procedure has been carried out with two commercial kit formulations for the preparation of $^{99m}$Tc-MDP and $^{99m}$Tc-MAG3 radiopharmaceuticals. The detailed procedures are reported in the following examples.

EXAMPLE 22

Preparation of [$^{188}$Re(MDP)]

0.2 mg of SnCl$_2$, dissolved in 0.5 mL of 20% aqueous acetic acid, 10.0 mg of γ-cyclodexttin 30.0 mg of sodium oxalate were added to a vial containing a commercial cold (i.e. non radioactive) kit formulation for the preparation of $^{99m}$Tc-MDP, followed by 0.250 mL of [$^{188}$ReO$_4$]$^-$ (50 MBq–500 MBq). The vial was kept at room temperature for 15 min. Yield>95%.

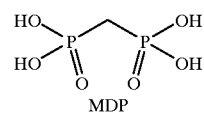

MDP

EXAMPLE 23

Preparation of [$^{188}$Re(O)(MAG3)]

0.2 mg of SnCl$_2$, dissolved in 0.5 mL of 20% aqueous acetic acid, 10.0 mg of γ-cyclodextrin and 5.0 mg of sodium oxalate were added to a vial containing a commercial cold kit formulation of $^{99m}$Tc-MAG3, followed by 0.250 mL of [$^{188}$ReO$_4$]$^-$ (50 MBq–500 MBq). The vial was heated at 100° C. for 15 min. Yield>95%.

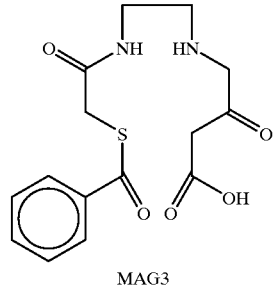

MAG3

The experimental results show that the method of the invention can be successfully applied to the labelling of various ligands., The yield of formation of the final complexes were always over 90%, and the labelling procedures have been carried out under very mild conditions. Based on experimental findings, the method appears to possess a wide applicability.

The role played by the host molecule appears to be that of displacing the equilibrium position of the reduction reaction towards the formation of the final product. This influence on the course of the reduction process can be envisaged by comparing the curves describing the disappearance of the activity of [$^{188}$ReO$_4$]$^-$ as a function of time when the reactions of formation of the complex [$^{188}$Re(O)(DMSA)]$^-$ were conducted both in the absence of γ-cyclodextrin and in the presence of 10 mg of this compound.

FIG. 1 illustrates the comparison between the curves obtained using only 0.2 mg of $SnCl_2$ and when 10.0 mg of γ-cyclodextrin were added to the preparation.

It is apparent from FIG. 1 that, at the same reaction time, the process using $SnCl_2$ in combination with γ-cyclodextrin is more displaced towards the formation of the product $[^{188}ReO(DMSA)_2]^-$ than that containing only $SnCl_2$. More specifically, on approaching the equilibrium at longer reaction times (180 min.), the residual percentage of $[^{188}ReO_4]^-$ remaining is always less when γ-cyclodextrin was present in the reaction procedure in comparison with the situation where it was not utilized. This effect has been observed with all the ligands employed in this study ranging from 50% to 15% depending on nature of the specific ligand and reaction conditions. It was particularly evident when the formation of the complex $[^{188}Re(DMSA)_2]^-$ was studied using 1.0 mg of $SnCl_2$ in combination with 10 mg of γ-cyclodextrin.

Figure 2:
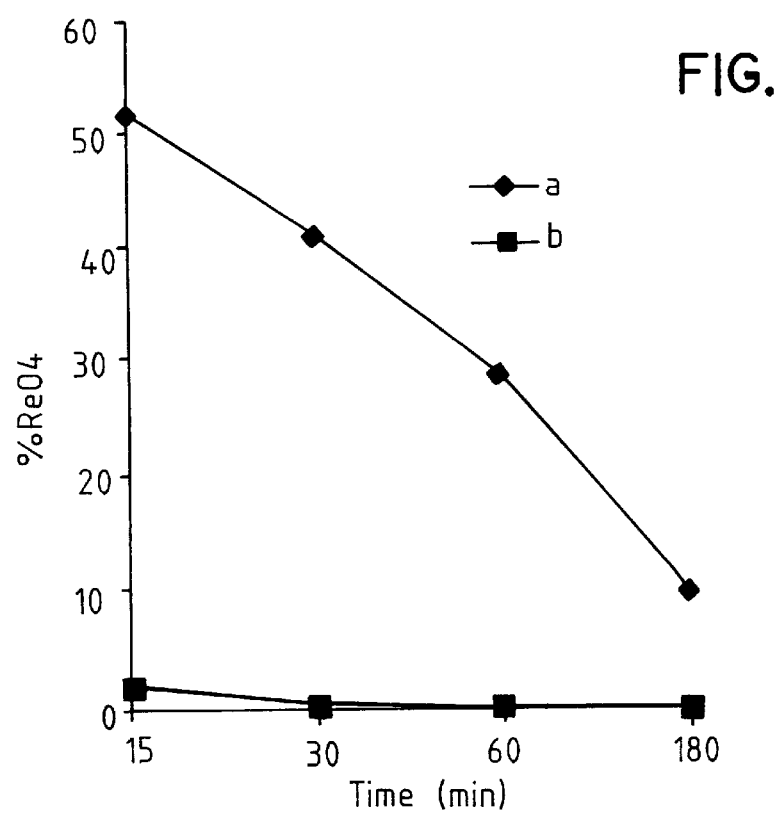

FIG. 2 reports the comparison between the time-activity curve obtained when only 1.0 mg of $SnCl_2$ were employed and that where 10.0 mg of γ-cyclodextrin were additionally used.

It is important to emphasize here that the effect of -displacing equilibrium exhibited by γ-cyclodextrin is maximum at longer reaction times (that is to say on approaching the-equilibrium of the reduction process), and is almost independent on the concentration of γ-cyclodextrin. These findings strongly support the description of the role of the host species forming supramolecular aggregates with some rhenium or technetium intermediate complexes formed during the course of the reduction process. In terms of the activated complex theory, therefore, the effect of the host molecule can be described as due to a lowering of the activation energy of the overall reduction process brought about by the supramolecular interaction. Accordingly the function of the host molecule may be defined as a catalyst or accelerator. The combination of $Sn^{2+}$, oxalate and γ-cyclodextrin appears to be the most efficient reduction procedure for $[^{188}ReO_4]$.

Figure 3:
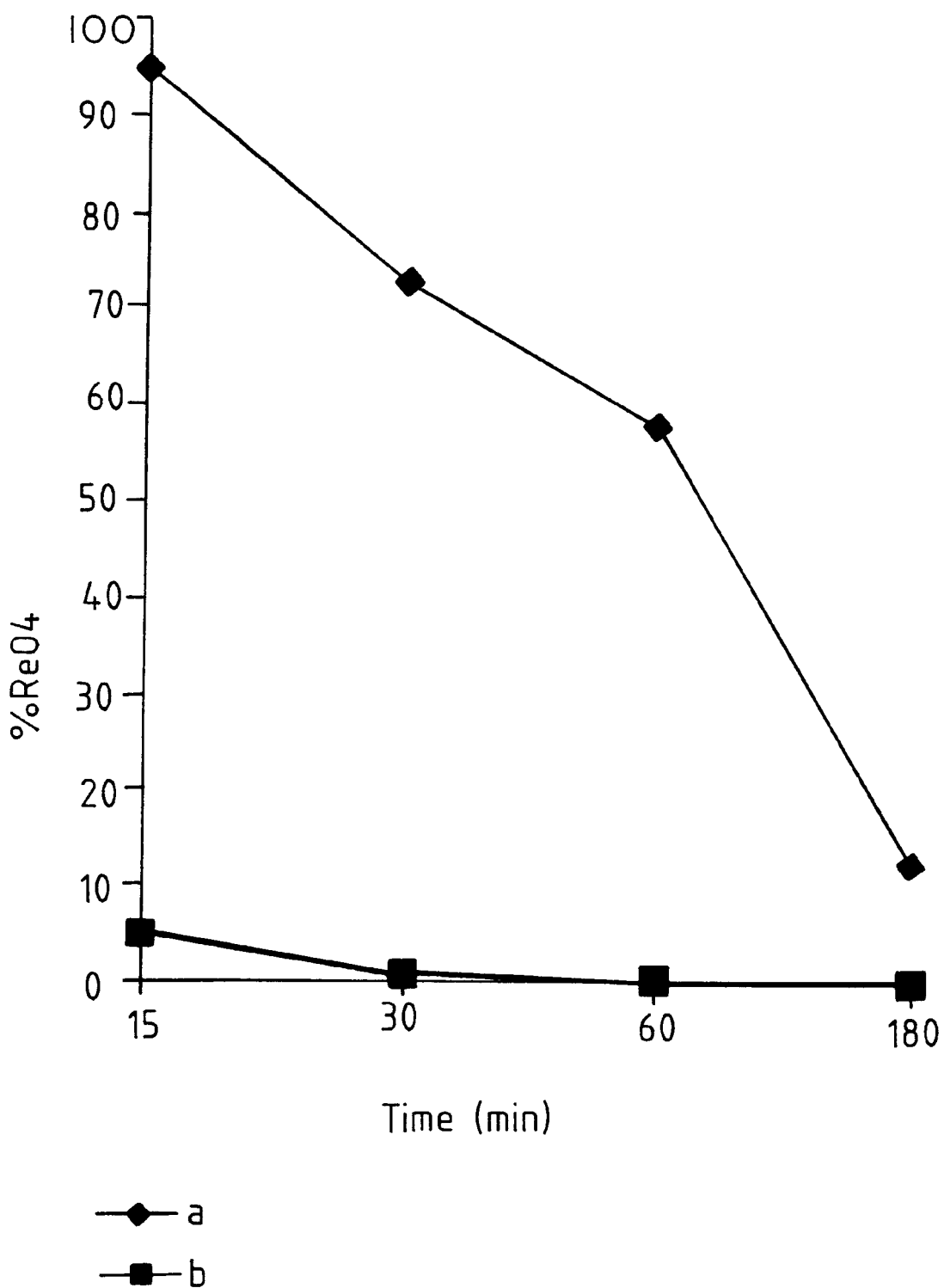

FIG. 3 compares the time-activity curve for-the reaction conducted using only 0.2 mg of SnCl, with that-obtained by including in the same reaction vial 6.0 mg of potassium oxalate and 10.0 mg of γ-cyclodextrin.

The invention also provides kits for the preparation of radiopharmaceutical products 'which include' one or more ligands able to bind to the radioactive rhenium or technetium metal, a reducing agent as described above, a compound selected from the cyclic oligosaccharides, crown ethers or cryptands and pharmaceutically acceptable vehicles and auxiliary substances such as antioxidants, stabilisers and thickeners. The components of the radiopharmaceutical kit may be combined in freeze-dried form or may be kept separate to be combined at the moment of use. The radiopharmaceutical composition is formed by the addition of the radioactive agent obtained from the generator.

What is claimed is:

1. A method for the reduction of an oxygenated compound of rhenium or technetium with a reducing agent, wherein the reduction reaction is carried out in the presence of a macromolecular compound selected from the group consisting of cyclic oligosaccharides, crown ethers, and cryptands, wherein said macromolecular compound is effective to displace the equilibrium of the reduction reaction toward the formation of a reduced species of said oxygenated compound and the reducing agent is selected from the group consisting of $Sn^{2+}$, $Fe^{2+}$, and $Cu^{1+}$ ions, and wherein the reducing agent is introduced into the reaction medium in the form of a halide, a phosphonate, or a salt of a polycarboxylic acid.

2. A method for the reduction of an oxygenated compound of rhenium or technetium with a reducing agent, wherein the reduction reaction is carried out in the presence of a macromolecular compound selected from the group consisting of crown ethers and cryptands, wherein said macromolecular compound is effective to displace the equilibrium of the reduction reaction toward the formation of a reduced species of said oxygenated compound.

3. The method according to claim 2 wherein the reduction is carried out in the presence of a ligand which can form a complex with the reduced species of the oxygenated compound of rhenium or technetium.

4. The method according to claim 2, in which the oxygenated compound is perrhenate ion or pertechnetate ion.

5. The method according to claim 2 wherein the reduction reaction is carried out in the presence of a secondary reducing agent comprising a polycarboxylic acid or metal salt thereof.

6. The method according to claim 2, in which the reducing agent is selected from the ions $Sn^{2+}$, $Fe^{2+}$, and $Cu^{1+}$.

7. The method according to claim 1, in which the polycarboxylic acid salt is selected from the group consisting of tarrates, citrates, oxalates, gluconates, and glucoheptonates.

8. The method according to claim 2, in which the reducing agent is selected from the group consisting of phosphines, alkali metal thiosulphites, dithionites, alkali metal dithionites, and alkali metal borohydride.

9. The method according to claim 3, in which the ligand is selected from the group consisting of phosphines, arsines, thiols, thioethers, isonitriles, amines, cyclic amines, polyamines, dithiocarbamates, dithiocarboxylates, Schiff bases, diaminodithiols, bis(amino)thiols, oximes, sugars, borates, amino acids, polyamino acids, peptides, peptides modified with phosphine groups and ligands, and mixtures thereof.

10. The method according to claim 9, in which the reduction reaction is carried out in the presence of a first ligand able to promote the stabilisation of the reduced state of the metal to form a complex which can undergo substitution reactions with other ligands, and in the presence of a second ligand which can undergo said substitution reaction with the first ligand to form a stable complex of the second ligand.

11. A method for the reduction of an oxygenated compound of rhenium or technetium with a reducing agent, characterised in that the reduction reaction is carried out in the presence of a macromolecular compound selected from the group consisting of cyclic oligosaccharides, crown ethers, and cryptands, wherein said macromolecular compound is effective to displace the equilibrium of the reduction reaction toward the formation of a reduced species of said oxygenated compound, and wherein the reduction reaction is carried out in the presence of a first ligand able to promote stabilisation of the reduced state of the metal to form a complex which can undergo a substitution reaction with other ligands, and in the presence of a second ligand which can undergo said substitution reaction with the first ligand to form a stable complex of the second ligand, said first ligand being a polycarboxylate compound.

12. The method according to claim 11, wherein the polycarboxylate compound comprises an oxalate or a citrate.

13. The method according to claim 2, wherein the reduction reaction is carried out at a pH of from 5 to 8.

14. A method of reducing a reaction time in a reaction for a reduction of perrhenate ion or pertechnetate ion in the presence of a reducing agent comprising using a macromolecular compound selected from the group consisting of crown ethers and cryptands.

15. A method for the reduction of an oxygenated compound of rhenium or technetium with a reducing agent, characterised in that the reduction reaction is carried out in the presence of a macromolecular compound selected from the group consisting of cyclic oligosaccharides, crown ethers, and cryptands, wherein said macromolecular compound is effective to displace the equilibrium of the reduction reaction toward the formation of a reduced species of said oxygenated compound, and wherein the reduction is carried out in the presence of a ligand selected from the group consisting of dimercaptosuccinic acid, 3,6-diaza-1,8-octanedithiol, 3,7-diaza-1,9-nonanedithiol, and tris(2-sulphonatophenyl)phosphine sodium salt.

* * * * *